(12) United States Patent
Leuschner et al.

(10) Patent No.: US 11,833,315 B2
(45) Date of Patent: Dec. 5, 2023

(54) ADDITIONAL FUNCTION OF A SAFETY DEVICE FOR INJECTION DEVICES

(71) Applicant: Gerresheimer Regensburg GmbH, Regensburg (DE)

(72) Inventors: Udo Leuschner, Regensburg (DE); Joerg Grosser, Lappersdorf (DE)

(73) Assignee: Gerresheimer Regensburg GmbH, Regensburg (DE)

( * ) Notice: Subject to any disclaimer, the term of this patent is extended or adjusted under 35 U.S.C. 154(b) by 63 days.

(21) Appl. No.: 17/201,349

(22) Filed: Mar. 15, 2021

(65) Prior Publication Data

US 2021/0283378 A1   Sep. 16, 2021

(30) Foreign Application Priority Data

Mar. 16, 2020  (EP) .................................... 20163366

(51) Int. Cl.
*A61M 25/06*   (2006.01)
*A61M 5/32*   (2006.01)

(52) U.S. Cl.
CPC ...... *A61M 25/0618* (2013.01); *A61M 5/3245* (2013.01)

(58) Field of Classification Search
CPC .......... A61M 25/0618; A61M 25/0631; A61M 25/0612; A61M 5/3243; A61M 5/3245; A61M 5/3216; A61M 5/3271; A61M 5/3272; A61M 2005/3217; A61M 2005/3247
See application file for complete search history.

(56) References Cited

U.S. PATENT DOCUMENTS 9,962,497 B2 *   5/2018   Takemoto ............. A61M 5/326
10,537,688 B2 *   1/2020   Wittland ............. A61M 5/3272
(Continued)

FOREIGN PATENT DOCUMENTS

CN    103025373    4/2013
CN    103732275    4/2014
(Continued)

OTHER PUBLICATIONS

Extended European Search Report in European Appln No. 20163366.6 dated Aug. 14, 2020, 16 pages (with English translation).
(Continued)

*Primary Examiner* — Kami A Bosworth
*Assistant Examiner* — Antarius S Daniel
(74) *Attorney, Agent, or Firm* — Fish & Richardson P.C.

(57) ABSTRACT

A safety device for injection devices is described. The safety device includes a sleeve extending along a longitudinal axis of the injection device's body, at least partially enclosing the injection device's needle and body, and including a guide slot; a collar attached to a distal end region of the body and locking the safety device in an axial direction; and a cap that can be arranged at least in part over the sleeve to prevent the body from moving relative to the sleeve. The cap includes a receptacle for the needle. The collar includes a guide pin that engages the guide slot. The collar can be arranged to rotate relative to the sleeve, and the receptacle of the cap can engage the collar and prevent the collar from rotating. The sleeve and the collar can each include a lock.

22 Claims, 13 Drawing Sheets

(56) References Cited

U.S. PATENT DOCUMENTS

Figure 1:
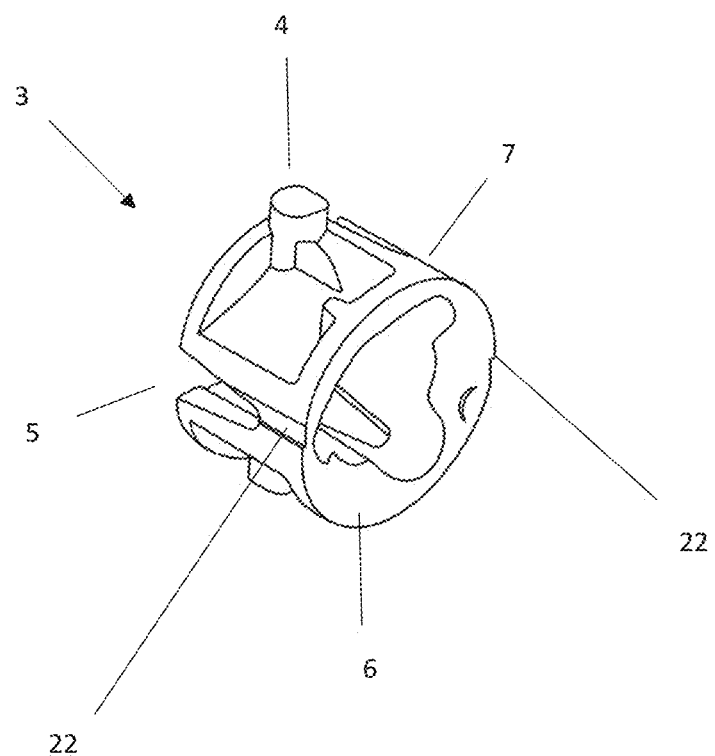

| | | | |
|---|---|---|---|
| 10,576,217 B2 * | 3/2020 | Wittland | ............ A61M 5/3272 |
| 2001/0004685 A1 | 6/2001 | Jansen et al. | |
| 2018/0021524 A1 | 1/2018 | Takemoto | |
| 2018/0326161 A1 | 11/2018 | Evans et al. | |
| 2020/0179614 A1 | 6/2020 | McElroy et al. | |

FOREIGN PATENT DOCUMENTS

| | | |
|---|---|---|
| CN | 103889484 | 6/2014 |
| DE | 102015110343 | 12/2016 |
| DE | 102015111835 | 1/2017 |
| DE | 102015111840 | 1/2017 |
| DE | 102016108870 | 11/2017 |
| EP | 2572745 | 3/2013 |
| EP | 3106191 | 12/2016 |
| EP | 3106193 | 12/2016 |
| EP | 3106194 | 12/2016 |
| EP | 3881881 | 9/2021 |
| JP | 2018-517470 A | 7/2018 |
| JP | 2018-518317 A | 7/2018 |

OTHER PUBLICATIONS

Extended European Search Report in European Appln No. 21189347.4 dated Nov. 22, 2021, 12 pages.
Office Action in Japanese Appln. No. 2021-040790, dated Sep. 13, 2022, 11 pages (with English translation).
CN Office Action in Chinese Appln. No. 202110231381.4, dated Jul. 21, 2022, 18 pages (with English translation).

* cited by examiner

ADDITIONAL FUNCTION OF A SAFETY DEVICE FOR INJECTION DEVICES

CROSS-REFERENCE TO RELATED APPLICATIONS

This application claims the benefit of priority to European Application Serial No. 20 163 366.6, filed on Mar. 16, 2020, which is hereby incorporated by reference in its entirety.

The present invention encompasses a safety device for injection devices, a method for mounting a safety device, an injection device safety system, and an injection device equipped with a safety device. Injection devices generally include a body or cartridge that holds a medicinal liquid, a hollow needle that is connected to the body for hypodermic injection of the medicinal liquid, and a piston or plunger for expelling the liquid through the needle. Examples of injection devices are syringes, injector pens, and autoinjectors.

In some cases, a collar of the syringe safety system comprises pins, for example guide pins, that move in a curved guide of the sleeve counter to a spring force and as far as a stop. The needle protrudes from a sleeve, and an injection can thus be administered. When the syringe is removed by the user, the spring relaxes again. The collar is moved with its pins into a locking position so that the syringe cannot be reused. Should the injection process be interrupted after the needle tip has left the sleeve, the safety system is intended to prevent reuse. In this case too, the collar is intended to be moved to the locking position by the spring force. The curved guide describes not only a movement direction in the vertical direction, but also in the horizontal direction. The spring is therefore tensioned and twisted. On account of the twisting, the collar is rotated back to the "starting position" as the spring relaxes. The safety system can thus return to the starting position and be used again.

Certain aspects of the concepts described herein can prevent reuse of the injection device or needle after the needle or needle tip has emerged from the sleeve or after the guide pin of the collar has reached a certain position on the curved track or guide slot of the sleeve. Implementations of the present disclosure are described in further detail herein with reference to a needle comprising a hollow shaft and a sharp tip designed to pierce the skin. It is contemplated, however, that implementations of the present disclosure can be realized with other devices that are designed to pierce the skin, for example, needles with a solid shaft or lancets.

Certain aspects can reduce or completely avoid the risk of the collar springing back to the starting position. These objects can, in certain instances, be achieved by the features of the claims.

In certain aspects, the sleeve and the collar of the safety device are each provided with a lock.

In certain aspects, the lock of the sleeve has at least one rib or shaft, which is arranged vertically or longitudinally along the length of the injection device. In some implementations, the sleeve has two opposite ribs. The collar is snapped over the ribs of the sleeve when pressed against a spring force by the lock. Fixing in a direction of rotation is effected in this way.

The ribs or shafts have flanks with different flank angles, which are formed in such a way that one flank angle is shallow and the other flank angle is steep. An outlet opening is located at the distal end of the sleeve. The proximal end of the sleeve is connected to the body of the injection device.

In some implementations, the lock of the collar has at least one protrusion on its lateral face with flanks, wherein the flanks have different flank angles, wherein one flank angle is shallow and the other flank angle is steep.

In some implementations, the collar and the sleeve rotate directly on the ribs and protrusions in only one direction, for example comparable to a ratchet function. The safety against reuse of the needle tip is ensured by the locking of the lock of the collar and sleeve.

The internal diameter of the sleeve and the external diameter of the collar can overlap in the regions of the protrusions of the collar and of the ribs of the sleeve. In some implementations, a region of the external diameter of the collar is not overlapped by the internal diameter of the sleeve, such that the ribs of the sleeve lie free.

The safety device can include at least one spring, which is operatively connected to the body of the injection device and counteracts the movement of the sleeve relative to the safety device, wherein the collar, when pressed against the spring force by the safety device, rotates on account of the predefined guide slot and snaps over the ribs of the sleeve by means of the lock.

On account of the flank angles of the sleeve and of the collar, a rotation of the collar is ruled out in the region of the guide slot that leads to a starting position. In the starting position, the collar is located at a proximal end of the sleeve. The outlet opening is located at a distal end of the sleeve.

In some implementations, the collar is held in the region of the guide slot that ends in the locking of the collar to the sleeve. By means of the spring force applied to the collar and to the ribs formed on the sleeve and to the protrusions on the collar, the protrusions of the collar are guided into the ribs of the sleeve and snapped into place. The sleeve has a guide slot in which at least one guide pin runs, as a result of which different positions of the sleeve can be realized. The snapping of the protrusions into the ribs takes place in a position of the guide slot when the needle tip has been moved so far in the distal direction in the sleeve that contamination of the needle tip can no longer be ruled out. As the guide pin moves back in the guide slot in the direction of the proximal end of the sleeve, the guide pin is held in the end position by the configuration of the guide slot. This avoids a situation in which the collar springs back into the starting position and the needle is possibly used again when the collar moves back to the proximal end of the sleeve.

Reuse of the injection device is thus prevented. Moreover, additional safety against reuse of the injection device is ensured by the lock of the sleeve and collar.

In some implementations, the collar is designed substantially as a hollow circular cylinder. In some implementations, the circular cylinder has a lateral face on which the at least one guide projection is formed. In some implementations, he at least one guide projection extends radially away from the lateral face. For example, the guide projection is designed as a circular cylinder or as a pin. Two diametrically opposite guide projections can be arranged on the lateral face. Accordingly, the sleeve would also have two diametrically opposite guide slots, in each of which a respective guide projection is guided. In certain aspects, the collar is moreover arranged to rotate in a circumferential direction on the distal end region of the body of the injection device. During use of the injection device, the injection device is pressed with the safety device against the skin of the patient. By the movement of the body of the injection device relative to the sleeve and the guiding of the guide projection in the guide slot, a rotation of the collar along a circumferential direction is brought about. The sleeve thus slides over the body of the injection device, as a result of which the needle passes through a corresponding opening in the sleeve. A rotation of the sleeve on the skin of the patient about the puncture site is thus avoided.

In certain aspects, the cap has a receptacle, in which the needle can be arranged. A receptacle of this kind ensures additional protection of the needle against damage and in particular against contamination.

In some implementations, the sleeve has a distal opening. For example, the internal diameter of the distal opening is at least in part greater than the external diameter of the receptacle, such that the receptacle can be arranged inside the sleeve.

In certain aspects, the receptacle can be brought into operative contact with the collar, as a result of which the collar can be locked in respect of a rotation. Such an operative contact can be, for example, a frictional contact. However, it would also be conceivable that the receptacle and the collar have a mutually corresponding lock that prevent a rotation of the collar.

In certain aspects, the cap and the sleeve have mutually complementary locking elements, such that the cap and the sleeve can be locked separately. It would be conceivable that a locking element has a predetermined breaking point that has to be broken open before use, in order to allow the cap to be pulled from the sleeve. However, it would also be conceivable that engagement of the locking elements is also permitted after the use of the injection device. This would allow the cap to be placed back firmly on the sleeve after the use of the injection device, as a result of which the sleeve would again be lockable with respect to the movement of the body of the injection device relative to the sleeve. Accordingly, the used injection device can be safely disposed of, with no further risk of injury.

In certain aspects, the cap comprises at least one wing-like element, which can be received in at least one recess of the sleeve. For example, the cap has two wing-like elements, which can be received diametrically in two respective recesses of the sleeve. Particularly preferably, the two wing-like elements are arranged diametrically opposite each other on the cap.

In certain aspects, at least one wing-like element can be brought into operative contact with the collar, as a result of which the collar can be locked in respect of a rotation. Such an operative contact can be, for example, a frictional contact. However, it would also be conceivable that the receptacle and the collar have a mutually corresponding lock that prevent a rotation of the collar.

In certain aspects, at least one locking element is arranged on the at least one wing-like element of the cap, which locking element can engage in at least one complementary locking element arranged in the at least one recess of the sleeve.

In some implementations, the cap is formed integrally with the receptacle. Such a design of the safety device has the advantage of cost-effective and straightforward production.

However, it is also conceivable that the cap has a distal opening, wherein the distal opening is designed as a recess in order to receive the receptacle. Thus, the cap and the receptacle can be produced from different materials. It would accordingly be conceivable to produce the receptacle from an elastic material, for example rubber. Such an elastic material helps reduce the risk of damaging the needle.

In some implementations, the safety device has at least one spring, which is operatively connected to the body of the injection device and counteracts the movement of the body relative to the safety device. Accordingly, the needle remains inside the sleeve until the intended use. During use, the sleeve has to be moved against the spring force so that the needle can pass through the opening of the sleeve. After use of the injection device, the sleeve, driven by the spring force of the spring, slides automatically back over the needle. By the guide projection being guided in the guide slot, the collar rotates counter to the circumferential direction. The user is thus protected against needlestick injuries from the used and contaminated needle. In some implementations, the spring comprises a helical spring. However, other spring types are also conceivable, for example leg springs or torsion springs. It would also be conceivable for the spring to be configured as an elastomer.

The spring can thus ensure that the needle can be returned safely into the safety device after use of the injection device, and the guide pin can be transferred automatically to the end position.

The spring can be embodied in different ways. In some implementations, the spring is a helical spring.

In certain aspects, the safety device is at least operatively connected to the body of the injection device by a collar. It is conceivable here that the guide pin/guide pins is/are arranged on the collar.

The collar is connected on the one hand to a needle attachment, which is connected to the body, and, on the other hand, to the safety device the at least one guide pin, since the guide pin is arranged inside the guide slot of the safety device.

The collar is particularly arranged inside a sleeve of the safety device. This sleeve also has the guide slot. In certain aspects, the safety device, in particular the sleeve, comprises two recesses, and the collar comprises two guide pins, wherein the recesses and the guide pins are formed lying opposite each other, as a result of which guiding can be ensured.

In some implementations, the spring is also arranged inside the sleeve and is can be secured in the sleeve, against falling out of the latter, by the collar.

Figure 2:
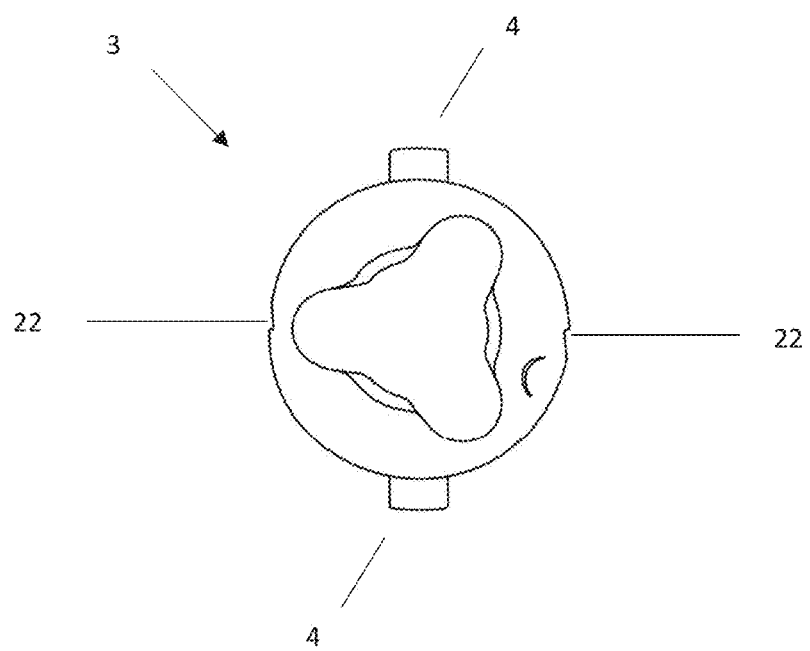
Figure 3:
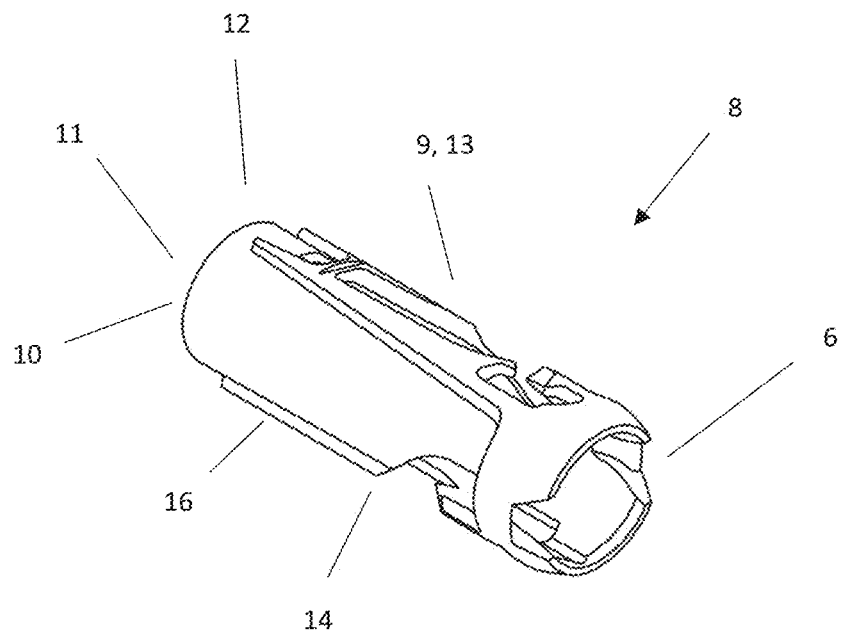
Figure 4:
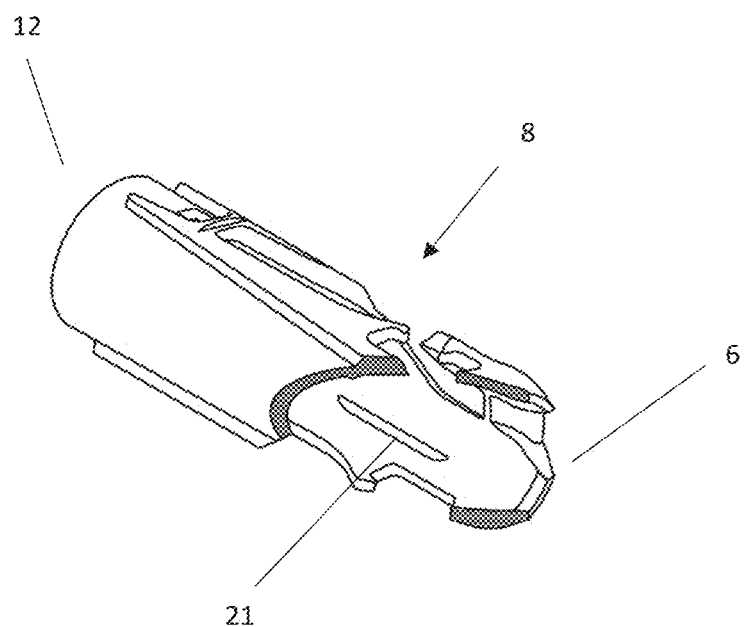
Figure 5:
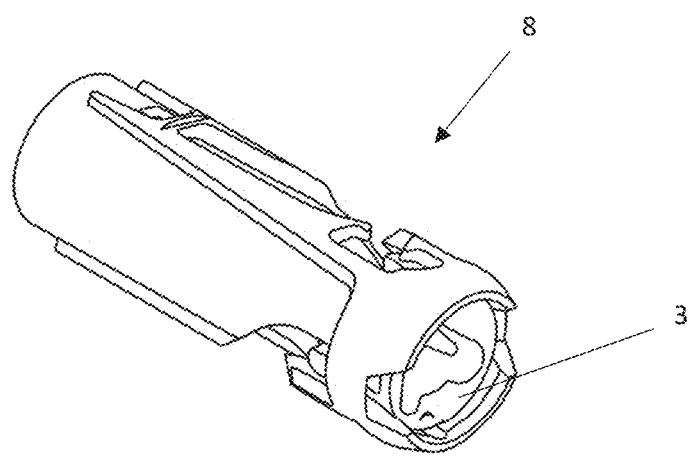
Figure 6:
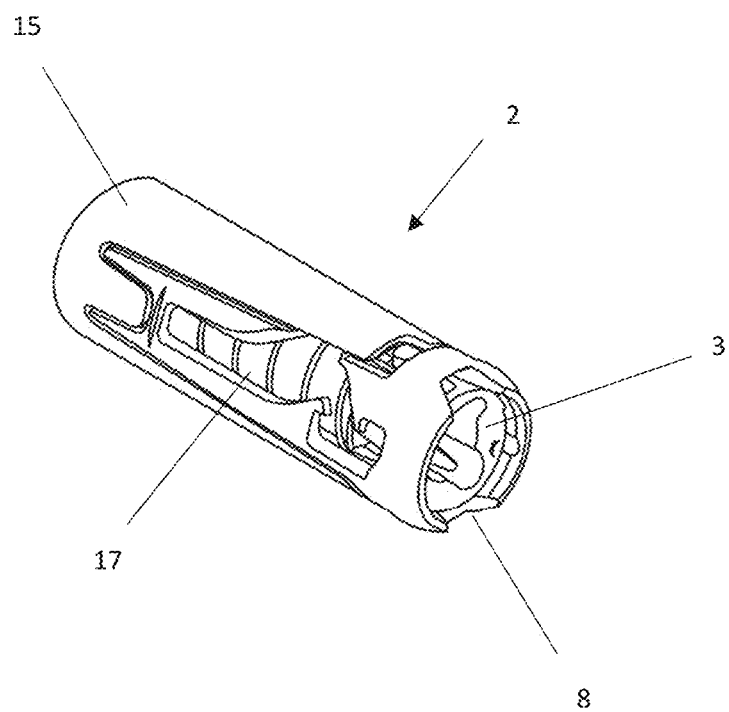
Figure 7:
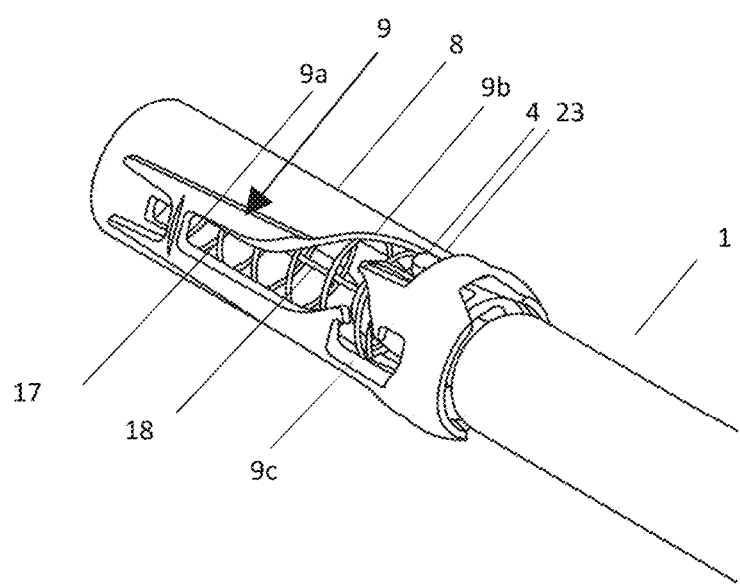
Figure 8:
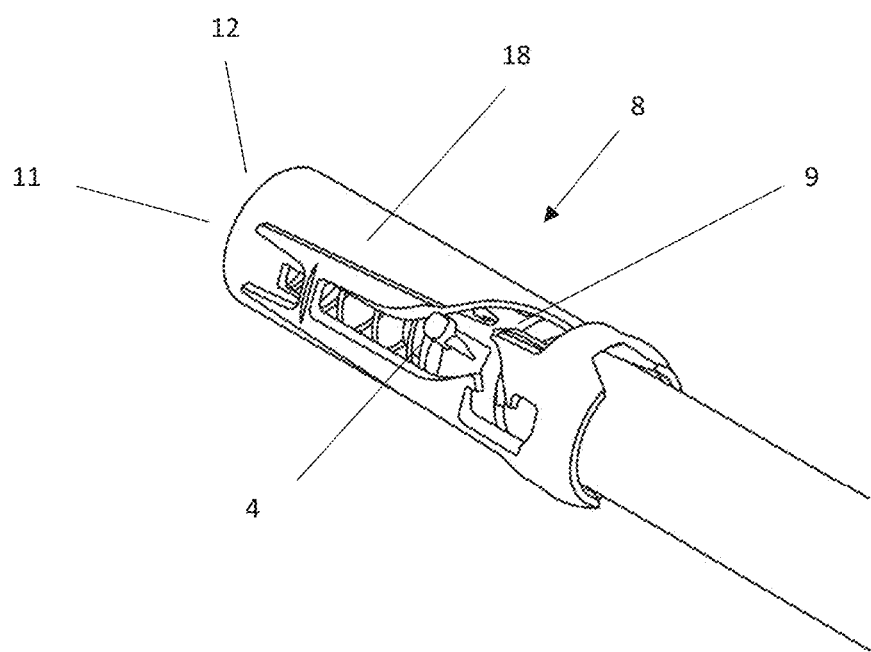
Figure 9:
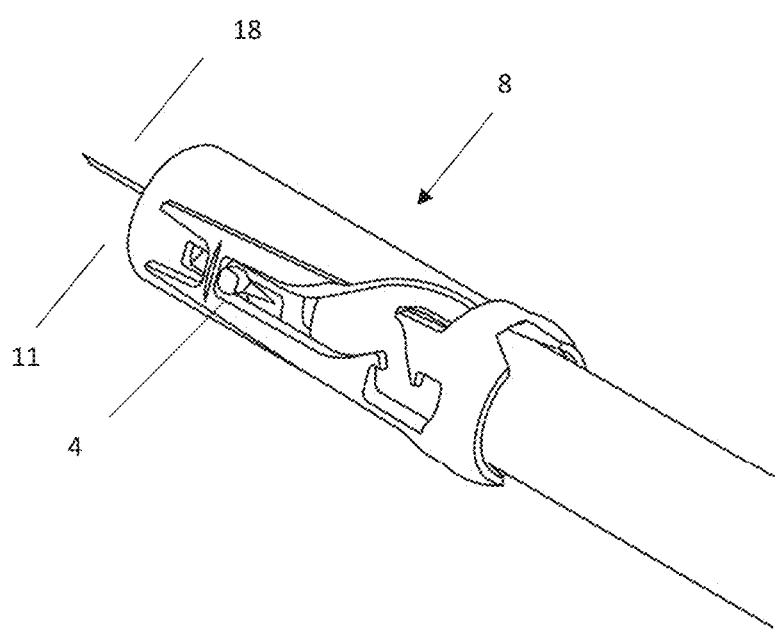
Figure 10:
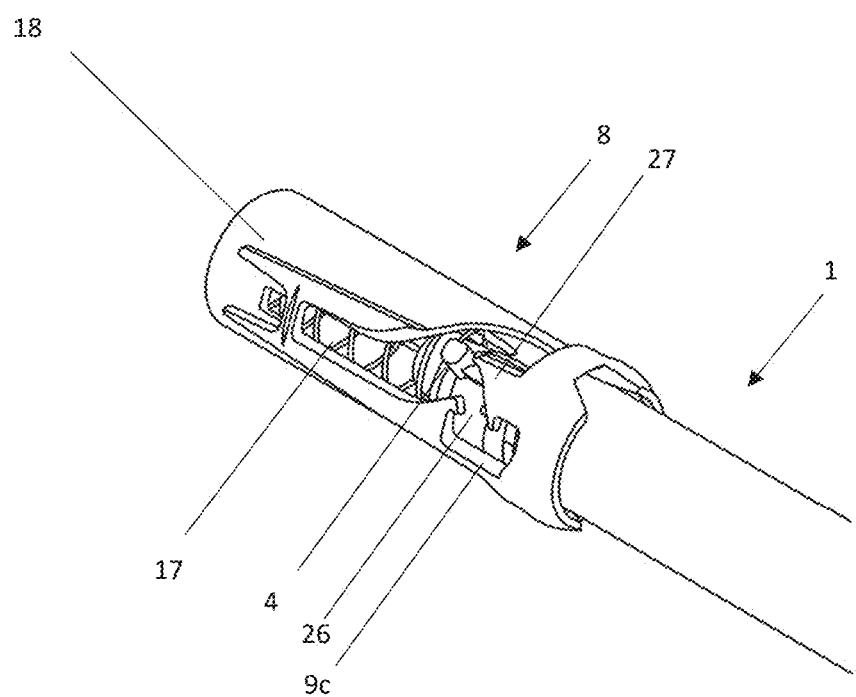
Figure 11:
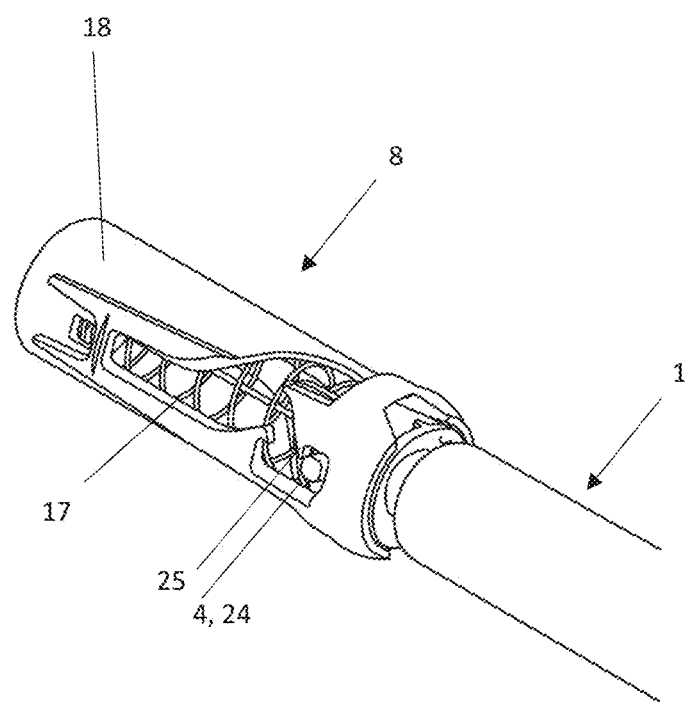
Figure 12:
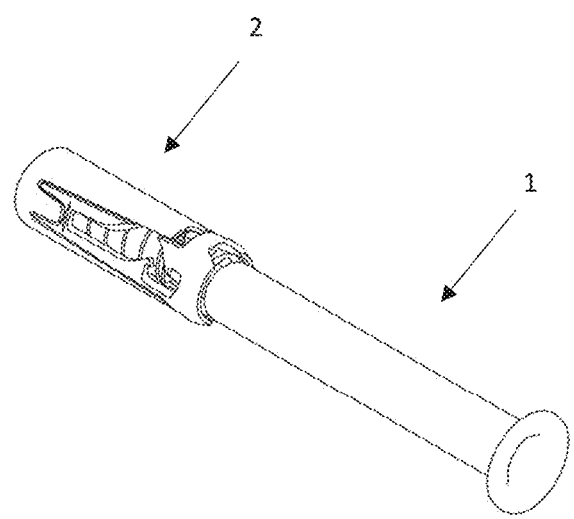
Figure 13:
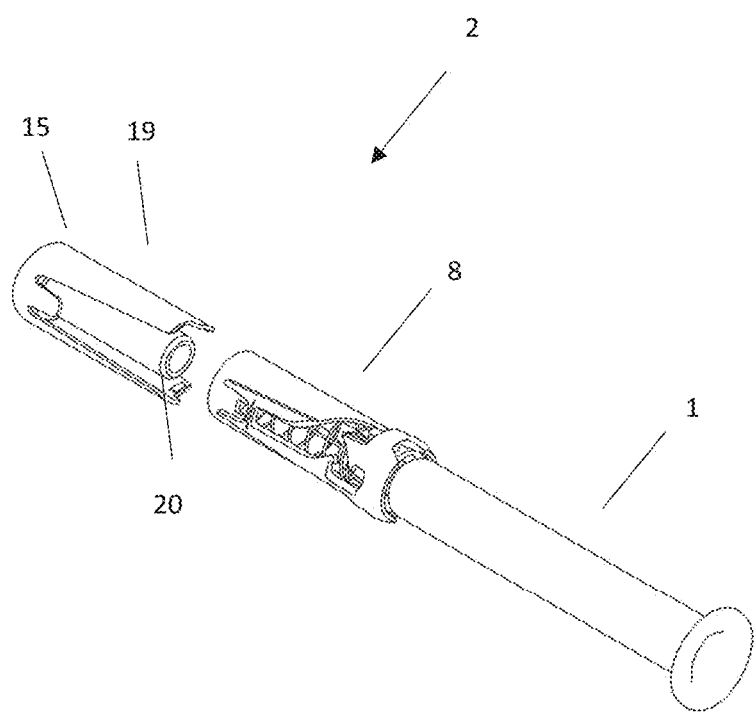

Implementations are explained in more detail below with reference to the accompanying drawings, in which:

FIG. 1 shows a perspective view of the collar;
FIG. 2 shows a plan view of the collar;
FIG. 3 shows a perspective view of the sleeve;
FIG. 4 shows a perspective view of the sleeve with partial sectioning;
FIG. 5 shows a perspective view of the sleeve with the collar;
FIG. 6 shows a perspective view of the sleeve and of the collar;
FIG. 7 shows a perspective view of the sleeve and syringe body;
FIG. 8 shows a perspective view of the sleeve with compressed spring force;
FIG. 9 shows a perspective view of the sleeve with syringe body, and the protruding needle;
FIG. 10 shows a perspective view of the sleeve with syringe body, and the retracted needle;
FIG. 11 shows a perspective view of the sleeve in a safety position;
FIG. 12 shows a syringe body with a safety device mounted thereon;
FIG. 13 shows a syringe body with a safety device mounted thereon and with the cap removed.

In the FIG. 1 to 13, a syringe is depicted as an example of an injection device. It is contemplated, however, that implementations of the present disclosure can be realized with other types of injection devices, such as autoinjectors or pen injectors.

FIG. 1 shows the collar 3 that connects the sleeve, and thus the safety device as a whole, to the syringe body. The collar 3 in the present case has substantially a cylindrical shape with an external diameter and an internal diameter, wherein the proximal end of the collar is designated by reference sign 6.

In the present case, a guide pin 4 is arranged on a lateral face 7 of the collar 3. This guide pin 4 can then be arranged in the guide slot of the sleeve and can be operatively connected thereto.

The collar 3 additionally has one or more recessed portions or cutouts 5, in the present case two cutouts 5.

The safety device comprising the sleeve, the collar 3 and the cap can be preassembled and is connectable as a whole to the syringe body by the collar 3.

FIG. 2 shows a plan view of the collar 3 with two guide pins 4 and ramps or protrusions 22 arranged on the lateral face 7 of the collar 3. The ramps or protrusions 22 have flanks with different flank angles, wherein one flank angle is shallow and forms an outer circumferential ramp surface adjacent to the protrusions, and the other flank angle is steep and forms a blocking surface that extends substantially radially with respect to the longitudinal axis of the syringe body.

FIG. 3 shows a perspective view of an important component of the safety device, namely the sleeve 8. The sleeve has a recess 13, which forms a guide slot 9 for guiding the guide pin 4 (not shown here). In some implementations, the guide slot 9 comprises a longitudinal guide slot portion 9a that extends substantially along the longitudinal axis of the body and a curved guide slot portion 9b that is arranged proximally from and communicates with the longitudinal guide slot portion, wherein the collar is arranged to rotate in a circumferential direction as the guide pin 4 translates along the curved guide slot portion (FIG. 7). In addition, the sleeve can have a clearance region 14. In the present case, the clearance region 14 serves the purpose of allowing a cap 15 (see FIG. 13) to be plugged on in a guided manner so as to increase the safety of the safety device. By the boundary 16 of the clearance region 14, the cap is at least in operative contact with the sleeve 8 and can be connected at least by force-fit engagement. The internal diameter 10 of the sleeve 8 is smaller than the external diameter of the cap. Moreover, the sleeve can have an outlet opening 11 at the distal end 12.

FIG. 4 shows the sleeve in a perspective view with partial sectioning such that a ridge or rib 21 is shown by partial sectioning of the sleeve 8. The rib 21 is arranged vertically or longitudinally along the syringe body on an inner circumferential surface of the sleeve 8. The ribs or shafts have flanks with different flank angles, wherein one flank angle is shallow and forms an inner circumferential sleeve surface adjacent to the rib 21, and the other flank angle is steep and forms a ridge surface that extends substantially radially with respect to the longitudinal axis of the syringe body. An outlet opening 11 is located at the distal end 12 of the sleeve 8. The proximal end 6 of the sleeve 8 is connected to the syringe body 1 (not shown in FIG. 4).

FIG. 5 shows the sleeve 8 with the collar 3. Here, the collar 3 is connected to the sleeve 8 by the guide pins.

FIG. 6 shows a perspective view of the sleeve 8 with the collar 3, a spring 17 and a cap 15. The cap 15 is described in more detail with reference to FIG. 13.

Referring to FIGS. 7 to 11, the safety device 2 is set out in detail, in particular the movement of the guide pin and of the syringe body 1 relative to the safety device 2, and the position of the needle 18. The arrangement composed of syringe body 1 and safety device 2 can be seen in a starting position in FIG. 7. A starting position is understood as an as yet unused syringe. The distal end 12 of the sleeve 8 can be placed directly onto the skin such that the outlet opening 11 comes into contact with the skin. If the syringe body 1 is now moved relative to the safety device 2 in the longitudinal direction, the guide pin is guided by the slot portion, as a result of which the collar 3 is moved. At the moment of transfer, the distal end of the needle 18 is thus at the level of the outlet opening 11. The needle 18 is thus about to emerge from the safety device 2, so that an injection is possible. The needle 18 can then be moved further out of the safety device 2 (see FIG. 9). When the injection has been carried out or the needle 18 has been moved out of the safety device 2, the user reduces the pressure on the syringe, as a result of which the syringe body 1 is moved relative to the safety device 2, counter to the longitudinal direction, by the spring force of the spring. The needle is thus moved back automatically into the safety device 2 by the spring.

FIG. 7 shows the sleeve 8 which, at its proximal end 6, is connected to the syringe body 1. In the starting position, the collar is located at a proximal end of the sleeve, and the guide pin 4 of the collar 3 is located in a starting position 23 in the curved guide slot portion 9b. The safety device has at least one spring 17, which is operatively connected to the syringe body and counteracts the movement of the sleeve 8 relative to the safety device, wherein the collar 3, when pressed against the spring force by the safety device, rotates on account of the predefined guide slot. By the application of a spring force against the collar 3, the collar or the guide pin 4 moves in the direction of the distal end 12 or the outlet opening 11 of the sleeve 8 (shown in FIG. 8). This has the effect that the needle or the needle 18 emerges from the outlet opening 11 of the sleeve 8 (shown in FIG. 9). When the needle 18 or the collar is pulled back, the guide pin 4 is locked in an end position 24 in the retaining portion 9c by the design of the guide slot 9, such that the collar 3 can no longer spring back to the starting position (shown in FIGS. 10 and 11). By the configuration of the flank angles of the ribs 21 of the sleeve and of the protrusions 22 of the collar, and by the spring force applied to the collar 3, the protrusions 22 are guided into the ribs 21 and snapped into place.

The sleeve has a guide slot 9 in which at least one guide pin 4 runs, as a result of which different positions of the sleeve 8 can be realized. The snapping of the protrusions 22 into the ribs 21 takes place in a position of the guide slot when the needle tip has been moved so far in the distal direction in the sleeve that a contamination of the needle tip can no longer be ruled out, for example, as the guide pin 4 leaves the curved guide slot portion 9b or as the guide pin 4 enters the longitudinal guide slot portion 9a. As the guide pin 4 moves back in the guide slot 9 in the direction of the proximal end 6 of the sleeve 8, the guide pin 4 is guided into an opening 26 that communicates the retaining portion 9c with the longitudinal guide slot portion 9a, e.g., by a bumper 27 disposed opposite the opening 26. The guide pin 4 is held in the end position 24 by the configuration of the guide slot, e.g. by a claw 25 provided in the retaining portion 9c. This prevents a situation in which the collar springs back into the starting position and the needle is possibly used again when the collar moves back to the proximal end of the sleeve.

Reuse of the syringe is thus prevented. Moreover, additional safety against reuse of the syringe is thus ensured by the lock of the sleeve and collar.

FIGS. 12 and 13 show a syringe body 1 with a safety device 2 mounted thereon. The safety device 2 here comprises, in addition to the cap 15, the sleeve and the collar 3, also a spring which is designed in the present case as a helical spring. In the present case, the cap 15 also comprises a receptacle 20 and a wing element 19, which device is designed to match the design of the clearance region 14. The receptacle 20 can be substantially cylindrical and is firmly connectable or connected to the cap 15, wherein the receptacle 20 can be designed in such a way that it can be plugged into the sleeve 8. This therefore signifies that an external diameter of the receptacle 20 corresponds at most to the internal diameter 10 of the sleeve. The dimensions of the safety device 2 are chosen such that the sleeve 8 has an internal diameter 10 greater than the diameter of the syringe body 1, such that the syringe body 1 is movable into the sleeve 8 during a forward longitudinal movement relative to the safety device 2. At the same time, the external diameter of the sleeve 8 or of the safety device 2 is chosen such that it corresponds at most to a maximum diameter of a holding device which is mounted on the proximal end of the syringe body 1 for the purpose of holding and securing the syringe.

Described implementations of the subject matter can include one or more features alone or in combination.

For example, in a first implementation, a safety device for an injection device having a body that extends along a longitudinal axis and a needle arranged at a distal end of the body, said safety device includes: a sleeve which extends along the longitudinal axis of the body, at least partially encloses the needle and the body, and comprises a guide slot; a collar which is attached to a distal end region of the body and locks the safety device in an axial direction, wherein the collar has a guide pin which engages the guide slot of the sleeve; and a cap which can be arranged at least in part over the sleeve and by which the sleeve can be locked in respect of a movement of the body relative to the sleeve, the cap comprising a receptacle in which the needle can be arranged; wherein the collar is arranged to rotate in a circumferential direction relative to the sleeve; wherein the receptacle of the cap can be brought into operative contact with the collar, as a result of which the collar can be locked in respect of the rotation; and wherein the sleeve and the collar are each provided with a lock.

In a second implementation, an injection device includes: a body that extends along a longitudinal axis, is configured to hold a liquid, and comprises a tip; a hollow needle connected to the tip of the body; an piston configured to expel the liquid stored in the body through the hollow needle; and a safety device that comprises: a sleeve which extends along the longitudinal axis of the body, at least partially encloses the needle and the body, and comprises a guide slot; a collar which is attached to a distal end region of the body and locks the safety device in an axial direction, wherein the collar has a guide pin which engages the guide slot of the sleeve; and a cap which can be arranged at least in part over the sleeve and by which the sleeve can be locked in respect of a movement of the body relative to the sleeve, the cap comprising a receptacle in which the needle can be arranged; wherein the collar is arranged to rotate in a circumferential direction relative to the sleeve; wherein the receptacle of the cap can be brought into operative contact with the collar, as a result of which the collar can be locked in respect of the rotation; and wherein the sleeve and the collar are each provided with a lock.

The foregoing and other described implementations can each, optionally, include one or more of the following features:

A first feature, combinable with any of the following features, wherein the lock of the sleeve has at least one rib or shaft, which is arranged longitudinally along a length of the body.

A second feature, combinable with any of the previous or following features, wherein the sleeve has at least two opposite ribs or shafts.

A third feature, combinable with any of the previous or following features, wherein the ribs or shafts have flanks with different flank angles, wherein one flank angle is shallow and the other flank angle is steep.

A fourth feature, combinable with any of the previous or following features, wherein an outlet opening is located at the distal end, and a proximal end is connected to the body.

A fifth feature, combinable with any of the previous or following features, wherein the lock of the collar has at least one protrusion, wherein the protrusion has flanks with different flank angles, and one flank angle is shallow and the other flank angle is steep.

A sixth feature, combinable with any of the previous or following features, wherein the collar has at least two opposite protrusions.

A seventh feature, combinable with any of the previous or following features, wherein an internal diameter of the sleeve and an external diameter of the collar overlap in the regions of the protrusions of the collar and of the ribs of the sleeve.

An eighth feature, combinable with any of the previous or following features, wherein the sleeve and the collar are configured to rotate relative to each other only in one direction at the ribs and protrusions.

A ninth feature, combinable with any of the previous or following features, wherein a region of the external diameter of the collar is not overlapped by the internal diameter of the sleeve, such that the ribs of the sleeve lie free.

A tenth feature, combinable with any of the previous or following features, further comprising at least one spring which is operatively connected to the body and counteracts a movement of the sleeve relative to the safety device, wherein the collar, when pressed against the spring force by the safety device, rotates on account of the predefined guide slot and snaps over the ribs of the sleeve.

An eleventh feature, combinable with any of the previous or following features, wherein, on account of the flank angles of the lock of the sleeve and of the collar, a rotation of the collar is blocked in the region of the guide slot that leads to a starting position.

A twelfth feature, combinable with any of the previous or following features, wherein the collar in the starting position is located at a proximal end of the sleeve, and an outlet opening is located at a distal end of the sleeve.

A thirteenth feature, combinable with any of the previous or following features, wherein the collar is held in the region of the guide slot that ends in the locking of the collar to the sleeve.

A fourteenth feature, combinable with any of the previous or following features, wherein the collar comprises a plurality of guide pins that each engage a respective guide slot of the sleeve.

In a third implementation, a method for mounting a safety device according to Claim 1 on a body of an injection device, comprises: (a) receiving a sleeve, a spring and a collar, (b) inserting the spring into an interior of the sleeve along a mounting direction, (c) inserting the collar into the interior of the sleeve along the mounting direction, (d) receiving the safety device, (e) mounting the safety device on the body by connecting the collar to the body; wherein the collar has a guide pin which engages a guide slot of the sleeve, wherein the safety device has a cap which can be arranged at least in part over the sleeve and by which the sleeve can be locked in respect of a movement of the body relative to the sleeve, the cap comprising a receptacle in which the needle can be arranged; wherein the collar is arranged to rotate in a circumferential direction at the distal end region of the body; wherein the receptacle of the cap can be brought into operative contact with the collar, as a result of which the collar can be locked in respect of the rotation; and wherein the sleeve and the collar are each provided with a lock.

LIST OF REFERENCE SIGNS

1: syringe body
2: safety device
3: collar
4: guide pin/guide projection
5: cutout
6: proximal end
7: lateral face
8: sleeve
9: guide slot
10: internal diameter
11: outlet opening
12: distal end of the sleeve
13: recess
14: clearance region
15: cap
16: boundary
17: spring
18: needle
19: wing element
20: receptacle
21: ribs
22: protrusions
23: starting position
24: end position
25: claw
26: opening
27: bumper

The invention claimed is:

1. A safety device for an injection device having a body that extends along a longitudinal axis and a needle arranged at a distal end of the body, said safety device comprising:
a sleeve which extends along the longitudinal axis of the body, at least partially encloses the needle and the body, and comprises a guide slot, the guide slot comprising:
a longitudinal guide slot portion that extends substantially along the longitudinal axis of the body, and
a curved guide slot portion that is arranged proximally from and communicates with the longitudinal guide slot portion;
a collar which is attached to a distal end region of the body and locks the safety device in an axial direction, wherein the collar has a guide pin which engages the guide slot of the sleeve; and
a cap which can be arranged at least in part over the sleeve and by which the sleeve can be locked in respect of a movement of the body relative to the sleeve, the cap comprising a receptacle in which the needle can be arranged;
wherein the collar is arranged to rotate in a circumferential direction relative to the sleeve as the guide pin translates along the curved guide slot portion;
wherein the receptacle of the cap can be brought into operative contact with the collar, as a result of which the collar can be locked in respect of the rotation; and
wherein the sleeve and the collar are each provided with a lock, the lock of the sleeve comprises a ridge arranged on an inner circumferential surface of the sleeve and defines a ridge surface that extends along the longitudinal axis of the body and substantially radially with respect to the longitudinal axis, and wherein the lock of the collar is configured to engage the ridge surface of the lock of the sleeve as the guide pin leaves the curved guide slot portion or as the guide pin enters the longitudinal guide slot portion to prevent the circumferential rotation of the collar relative to the sleeve.

2. The safety device according to claim 1,
wherein the lock of the collar comprises a ramp arranged on an outer circumferential surface of the collar that comprises a longitudinal axis that extends along the longitudinal axis of the body,
wherein the ridge and the ramp are arranged to engage as the guide pin translates along the guide slot.

3. The safety device according to claim 2, wherein, the ridge of the lock of the sleeve and the ramp are configured to be brought into engagement as the guide pin leaves the curved guide slot portion and enters the longitudinal guide slot portion to prevent circumferential rotation of the collar relative to the sleeve.

4. The safety device according to claim 3, wherein the ridge of the sleeve and the longitudinal guide slot portion substantially overlap along the longitudinal axis of the body.

5. The safety device according to claim 2, wherein the ridge of the sleeve and the ramp are configured to be brought out of engagement as the guide pin leaves the curved guide slot portion and enters the longitudinal guide slot portion.

6. The safety device according to claim 5, wherein the ridge of the lock of the sleeve and the curved guide slot portion substantially overlap along the longitudinal axis of the body.

7. The safety device according to claim 2, wherein the ramp defines a blocking surface that extends substantially radially with respect to the longitudinal axis of the body, and wherein bringing the ridge surface and the blocking surface into abutment engages the ridge and the ramp.

8. The safety device according to claim 7, wherein the sleeve comprises an inner circumferential sleeve surface adjacent to the ridge and the collar comprises an outer circumferential ramp surface adjacent to the ramp, wherein the circumferential sleeve surface and the circumferential ramp surface are arranged for sliding engagement as the collar rotates in a circumferential direction.

9. The safety device according to claim 2, wherein an internal diameter defined by the ridge is less than an external diameter defined by the ramp.

10. The safety device according to claim 9, wherein the outer circumferential surface of the collar comprises a recessed portion that is recessed with respect to the ramp.

11. The safety device according to claim 1, further comprising a spring that is operatively connected to the body via the collar and counteracts a relative movement between the sleeve and the body along the longitudinal axis of the body, wherein the spring is arranged to apply a torsion force to the collar as the collar compresses the spring.

12. The safety device according to claim 11, wherein the respective locks of the sleeve and of the collar are configured to block movement of the guide pin into the curved guide slot portion as the spring relaxes.

13. The safety device according to claim 11, wherein the spring is configured to bias the collar in a starting position in which the guide pin is arranged at a proximal end of the curved guide slot portion.

14. The safety device according to claim 12, wherein the guide slot further comprises a retaining portion that is arranged proximally from and communicates with the longitudinal guide slot portion, wherein the guide slot and the respective locks of the sleeve and of the collar are configured to guide the guide pin into the retaining portion as the spring relaxes.

15. The safety device according to claim 14, wherein the retaining portion of the guide slot comprises a claw arranged to engage a circumferential surface of the guide pin.

16. The safety device according to claim 14, wherein the retaining portion comprises an opening that communicates the retaining portion with the longitudinal guide slot portion, and wherein the guide slot comprises a bumper disposed opposite the opening of the retaining portion and configured to interface with the guide pin to guide the guide pin into the retaining portion.

17. A method for mounting the safety device according to claim 1 on the body of the injection device, comprising:
   a. receiving the sleeve, a spring and the collar,
   b. inserting the spring into an interior of the sleeve along a mounting direction,
   c. inserting the collar into the interior of the sleeve along the mounting direction,
   d. receiving the safety device, and
   e. mounting the safety device on the body by connecting the collar to the body;
   wherein the collar is arranged to rotate in a circumferential direction at the distal end region of the body.

18. An injection device comprising:
   a body that extends along a longitudinal axis, is configured to hold a liquid, and comprises a tip;
   a hollow needle connected to the tip of the body;
   a piston configured to expel the liquid stored in the body through the hollow needle; and
   a safety device that comprises:
      a sleeve which extends along the longitudinal axis of the body, at least partially encloses the needle and the body, and comprises a guide slot, the guide slot comprising:
         a longitudinal guide slot portion that extends substantially along the longitudinal axis of the body, and
         a curved guide slot portion that is arranged proximally from and communicates with the longitudinal guide slot portion;
      a collar which is attached to a distal end region of the body and locks the safety device in an axial direction, wherein the collar has a guide pin which engages the guide slot of the sleeve; and
      a cap which can be arranged at least in part over the sleeve and by which the sleeve can be locked in respect of a movement of the body relative to the sleeve, the cap comprising a receptacle in which the needle can be arranged;
   wherein the collar is arranged to rotate in a circumferential direction relative to the sleeve as the guide pin translates along the curved guide slot portion;
   wherein the receptacle of the cap can be brought into operative contact with the collar, as a result of which the collar can be locked in respect of the rotation; and
   wherein the sleeve and the collar are each provided with a lock, the lock of the sleeve comprises a ridge arranged on an inner circumferential surface of the sleeve and defines a ridge surface that extends along the longitudinal axis of the body and substantially radially with respect to the longitudinal axis, and wherein the lock of the collar is configured to engage the ridge surface of the lock of the sleeve as the guide pin leaves the curved guide slot portion or as the guide pin enters the longitudinal guide slot portion to prevent the circumferential rotation of the collar relative to the sleeve.

19. The injection device according to claim 18, wherein the lock of the collar comprises a ramp arranged on an outer circumferential surface of the collar that comprises a longitudinal axis that extends along the longitudinal axis of the body, wherein the ridge and the ramp are arranged to engage as the guide pin translates along the guide slot.

20. The injection device according to claim 18, further comprising a spring that is operatively connected to the body via the collar and counteracts a movement of the body along its longitudinal axis relative to the safety device, wherein the spring is arranged to apply a torsion force to the collar when the collar compresses the spring.

21. The injection device according to claim 20, wherein the respective locks of the sleeve and of the collar are configured to block movement of the guide pin into the curved guide slot portion as the spring relaxes.

22. The injection device according to claim 21, wherein the guide slot further comprises a retaining portion that is arranged proximally from and communicates with the longitudinal guide slot portion, wherein the guide slot and the respective locks of the sleeve and of the collar are configured to guide the guide pin into the retaining portion as the spring relaxes.

* * * * *